US008253117B2

United States Patent
Gunji

(10) Patent No.: US 8,253,117 B2
(45) Date of Patent: Aug. 28, 2012

(54) FLUORESCENCE DETECTOR

(75) Inventor: Masahide Gunji, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 237 days.

(21) Appl. No.: 12/851,440

(22) Filed: Aug. 5, 2010

(65) Prior Publication Data

US 2011/0042581 A1 Feb. 24, 2011

(30) Foreign Application Priority Data

Aug. 19, 2009 (JP) .................................. 2009-189666

(51) Int. Cl.
*H05B 33/00* (2006.01)

(52) U.S. Cl. .................................................. 250/484.2

(58) Field of Classification Search ............... 250/484.4, 250/458.1, 459.1

See application file for complete search history.

(56) References Cited

U.S. PATENT DOCUMENTS

| | | | | |
|---|---|---|---|---|
| 6,316,774 | B1 * | 11/2001 | Giebeler et al. ........... | 250/458.1 |
| 6,809,324 | B1 * | 10/2004 | Schmidt ..................... | 250/459.1 |
| 7,361,472 | B2 * | 4/2008 | Yguerabide et al. ........... | 435/7.1 |
| 2004/0061072 | A1 * | 4/2004 | Gu et al. .................... | 250/458.1 |
| 2004/0130715 | A1 * | 7/2004 | Dosaka et al. ................ | 356/317 |
| 2005/0168741 | A1 * | 8/2005 | Banks ........................... | 356/417 |

FOREIGN PATENT DOCUMENTS

JP 2008-116424 5/2008

\* cited by examiner

*Primary Examiner* — Kiho Kim

(74) *Attorney, Agent, or Firm* — DLA Piper LLP (US)

(57) ABSTRACT

A fluorescence detector is provided to improve the non-linearity relationship between concentration and fluorescence intensity for a high specimen concentration. The detector improves the dynamic range of the measurements. For a high concentration of the specimen, a light beam restriction unit is used so that only the fluorescence being emitted from a region close to the incident end of the excitation light is condensed by the condensing lens and led to the fluorescence side spectrometer and detected. Because the fluorescence emitted from a region after the passage of the excitation light through a specimen solution as well as its strong absorption by the specimen solution is not reflected in the measurement result, the linearity of the relationship between concentration and fluorescence intensity is improved despite the reduction in the fluorescence quantity. For a low specimen concentration, the light beam restriction unit is used to improve sensitivity.

3 Claims, 4 Drawing Sheets

FLUORESCENCE DETECTOR

TECHNICAL FIELD

The present invention relates to a fluorescence detector that detects fluorescence emitted by a specimen when irradiated with an excitation light and primarily used with liquid chromatography, flow injection analyzers and the like.

BACKGROUND ART

Usual fluorescence detectors are constructed so that a specimen cell containing a specimen solution to be measured is irradiated with an excitation light of a specific wavelength extracted from spectrometer at the an excitation side. The fluorescence that is emitted by the specimen solution is passed through a spectrometer at the fluorescence side, the wavelength of the fluorescence is dispersed, and the fluorescence is introduced to a photodetector where the fluorescence is detected. Ordinarily, a rectangular cell made of quartz glass and the like is used as the specimen cell. However, a flow cell is used when the detector is used with liquid chromatography or a flow injection analyzer.

FIG. 5 shows a schematic view of an optical system of a typical fluorescence detector (see for example Patent Literature 1). A specimen solution S, for example, a solution that has passed through a column of a liquid chromatograph, is made to flow through flow cell 3 made of a transparent material such as quartz glass. The excitation side spectrometer 2 extracts light with a specific wavelength from the light that is emitted by a light source unit 1. The light that is extracted is irradiated onto the flow cell 3 as excitation light Lex. The target component in the specimen solution is excited by the excitation light Lex and emits fluorescence Lm which passes through the flow cell 3 and reaches the fluorescence side spectrometer 4. Fluorescence with a specific wavelength is extracted by the fluorescence side spectrometer 4, and the fluorescence intensity is detected by detector 5.

With the afore-described configuration, as the excitation light Lex that is incident on the flow cell 3 passes through the specimen solution S, it is absorbed and attenuated by the specimen solution S. This means that fluorescence Lm that is generated at a point in the flow cell 3 that is more distally located in the longitudinal direction of the flow cell 3 (i.e., the fluorescence Lm that is generated at a position further away from the point of incidence of the excitation light Lex) is going to be less intense than the fluorescence Lm that is generated at a point more proximal (i.e., at a point closer to the point of incidence of the excitation light Lex). The absorption and attenuation of the excitation light Lex by the specimen solution S is greater as the specimen concentration increases. This means that as the specimen concentration increases, the linearity of the relationship between specimen concentration and the detected fluorescence intensity degrades. FIG. 6 is a schematic graph showing the relationship between specimen concentration and fluorescence intensity. The graph shows an increasing deviation of the dotted line from the straight line with increasing specimen concentration.

With a fluorescence detector, the general practice is to use the results of the measurement of a standard specimen of a known concentration to prepare a calibration curve in advance, and to refer to the calibration curve to determine the specimen concentration of an unknown specimen. Ordinarily, a calibration curve is prepared based on the assumption that the relationship between specimen concentration and fluorescence intensity can be linearly approximated. This means that a poor linearity in the relationship between the two such as the afore-described degrades the accuracy of the calculated concentration. In particular, since the fluorescence intensity of a specimen tends to become saturated at higher concentrations, the concentration value becomes less accurate as the concentration rises. The end result is an insufficient dynamic range of the measurements.

PRIOR ART LITERATURE

Patent Literature

Patent Literature 1: Unexamined Patent Application Publication 2008-116424

SUMMARY OF THE INVENTION

Problems to Be Solved by the Invention

The present invention was made for the purpose of solving the afore-described problems, and it is the object of the present invention to provide a fluorescence detector that improves the linearity of the relationship between specimen concentration and fluorescence intensity even for high specimen concentrations and thus improve the dynamic range of the measurements.

Means for Solving the Problems

The present invention which has been made for solving the afore-described problems is a fluorescence detector comprising a specimen cell that holds a specimen therein, an excitation optical system that irradiates said specimen cell with an excitation light, and a fluorescence measurement optical system that detects the fluorescence that is emitted by the specimen in response to the excitation light, the fluorescence detector including a fluorescence adjustment optical system wherein a light beam restriction means that is installed close to the specimen cell so as to block the fluorescence that is emitted by the specimen but does not pass through the aperture and having an aperture of a predetermined length in the passage direction of the excitation light in a specimen cell and a condensing means that condenses the fluorescence that passes through the aperture of the light beam restriction means and leads the fluorescence to a fluorescence measurement optical system are provided as a pair and further including a mechanism for replacing or switching the fluorescence adjustment optical system so that the length of the aperture can be selected from any one of at least 2 types or more.

Here, the excitation optical system includes a light source, an excitation side spectrometer and the like, and the fluorescence measurement optical system includes a fluorescence side spectrometer, a photodetector (photomultiplier tube and the like) and the like. The specimen cell may be a flow cell through which a specimen solution flows or may be a rectangular cell and the like that hold a specimen solution. Furthermore, the specimen cell can be one that allows the excitation light coming from the excitation optical system to pass through the specimen solution only in one direction or may be constructed with a mirror that is positioned at the end opposite to the end where the excitation light becomes incident so that the excitation light that passes through the specimen solution is reflected by the mirror and passes once again through the specimen solution in the opposite direction (i.e., so that the excitation light travels through the specimen solution back and forth).

With the fluorescence detector according to the present invention, the light beam restriction means has an aperture which, regardless of the aperture length, can allow the fluorescence that is emitted from the incidence end side of the excitation light to said specimen cell to pass through the aperture. Furthermore, the condensing means has different optical properties and optical layout so that the incident light [whose attributes may] differ depending on the length and position of the aperture is correctly led to the fluorescence measurement optical system. As one example, a condensing lens can be used as the condensing means.

With fluorescence analysis that is performed using a fluorescence detector according to the present invention, if it is known that the range of specimen concentration of a specimen that is to be measured is generally at high, the person performing the analysis performs the measurement using a fluorescence adjustment optical system that includes a light beam restriction means of a relatively short aperture length. To explain, a calibration curve is prepared by measuring a specimen of a known concentration using an apparatus that includes the fluorescence adjustment optical system. The calibration curve is then used to perform a quantitative analysis on the unknown specimen. By using a light beam restriction means with a short aperture length, the fluorescence that is emitted in region close to the incident end of the excitation light to the specimen cell (i.e., the fluorescence that is emitted in regions where enough fluorescence is generated by the excitation light) is allowed to pass through the aperture, but fluorescence that is emitted in regions located far away from the incident end of the excitation light is blocked. This means that fluorescence whose change in intensity is minimal with respect to changes in specimen concentration is not reflected in the measurement result which consequently improves the linearity of the relationship between fluorescent intensity and specimen concentration. This improves the accuracy of the calculated concentration in a high concentration range.

Because a portion of the fluorescence is blocked, the efficiency with which the fluorescence is used is reduced. However, since the fluorescence that passes through the aperture is efficiently led to the fluorescence measurement optical system by the condensing means, there is no significant drop in the amount of fluorescence that becomes incident to the fluorescence measurement optical system even when compared to the case where the aperture length is large. This allows measurements to be made with sufficient sensitivity.

On the other hand, if it is known that the range of specimen concentration of the specimen that is to be measured is generally low, the person performing the analysis can perform the measurement using a fluorescence adjustment optical system that includes a light beam restriction means with a relatively long aperture length. In this case, in contrast to the situation where a fluorescence adjustment optical system includes a light beam restriction means of a short aperture length, even though the linearity of the relationship between specimen concentration and fluorescence intensity is reduced, so long as the concentration range is low, the range where the linearity is high can be used. Furthermore, since the fluorescence can be used with a high efficiency, specimens with a low concentration can be measured with a high sensitivity.

One preferable mode of a fluorescence detector according to the present invention is to construct the fluorescence adjustment optical system as an integral component so that the replacement of that component results in the selection of at least 2 types or more of aperture length. To explain, this is a construction wherein a light beam restriction means with a predetermined aperture length and a condensing means whose optical properties are adjusted for the aperture length are constructed as an integral component.

With this configuration, other than the fluorescence adjustment optical system component that is an integrated component, other components such as the excitation optical system, fluorescence measurement optical system, specimen cell and the like are commonly used so that measurements suitable for the specimen concentration can be performed simply by replacing the fluorescence adjustment optical system component that is installed. This simplifies the operation for the person performing the analysis and eliminates cumbersome adjustment work and the like.

Effects of the Invention

As afore-described, the fluorescence detector according to the present invention improves the linearity of the relationship between specimen concentration and fluorescence intensity even when the specimen concentration is high, thus improving the accuracy of the specimen concentration that is calculated based on a calibration curve. A result of this is that the upper limit of the measurable specimen concentration is raised which in turn means an improved dynamic range of the measurements.

EMBODIMENTS OF THE INVENTION

Figure 1A:
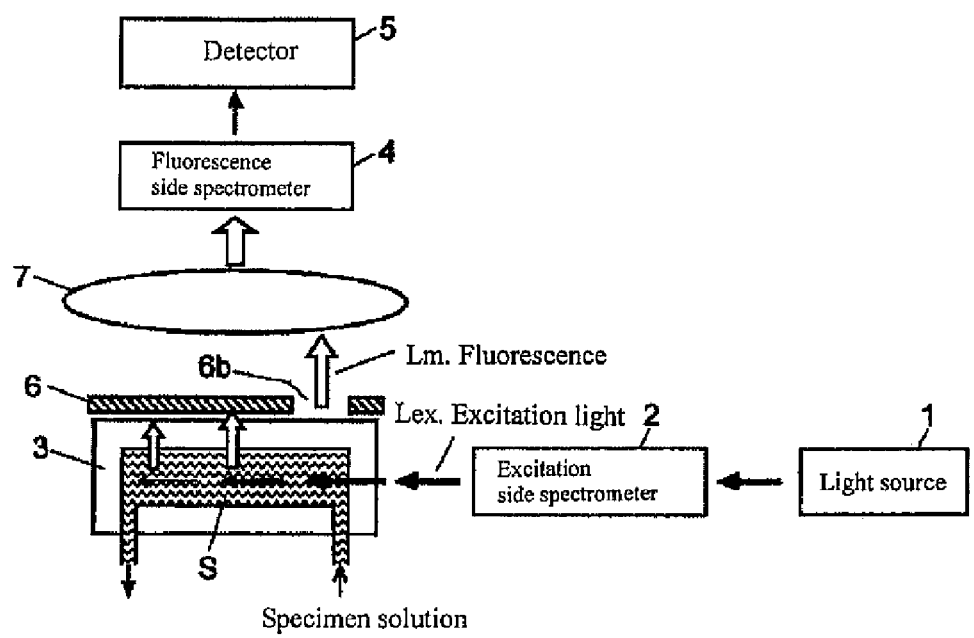
FIGS. 1A and 1B shows a schematic views of the optical system in one embodiment of a fluorescent detector according to the present invention.
Figure 1B:
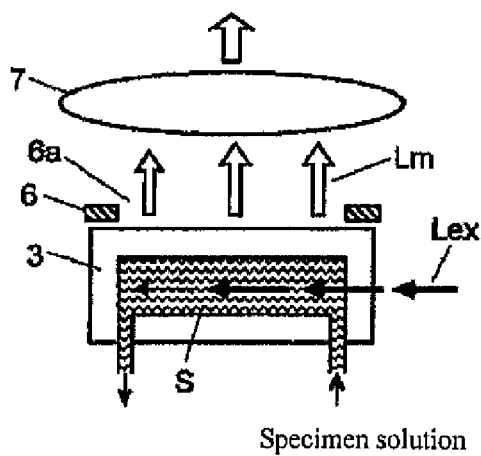
Figure 2:
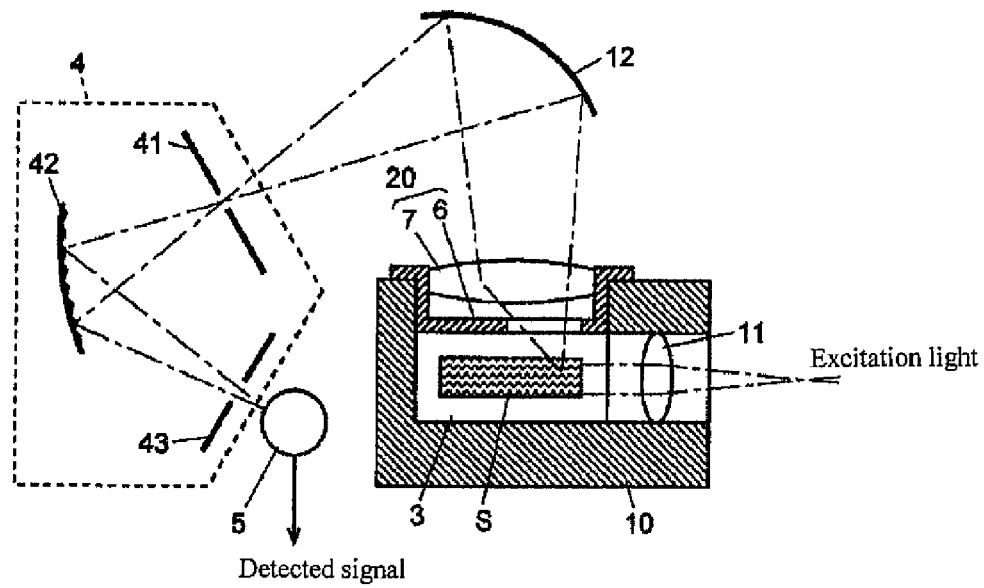
FIG. 2 shows a specific configuration of the optical system of FIG. 1.

One embodiment of a fluorescence detector according to the present invention is described next with reference to the attached figures. FIG. 1A and FIG. 1B shows a schematic views of the optical system of a fluorescence detector of the present embodiment. FIG. 2 shows a specific configuration of the optical system in a fluorescence detector of the present embodiment. FIGS. 3A-3D shows an external views and a sectional views of the fluorescence adjustment optical unit shown in FIG. 2.

Figure 5:
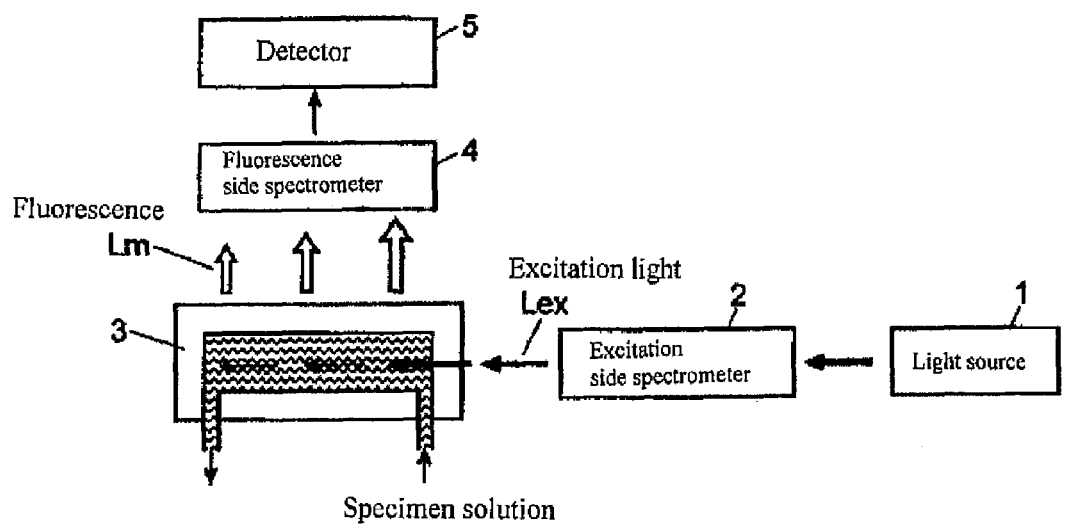
FIG. 5 shows a schematic view of the optical system in a typical previous fluorescence detector.
Figure 6:
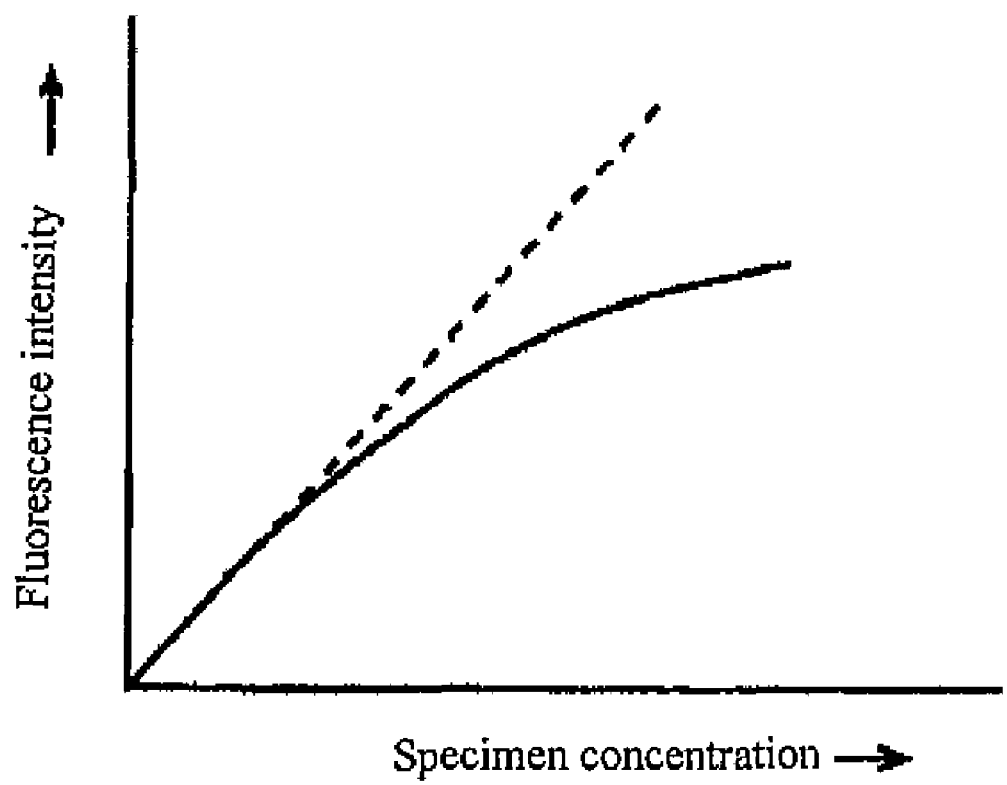
FIG. 6 is a graph showing the relationship between specimen concentration and fluorescence intensity in a previous fluorescence detector.

The same reference numbers are used for the same component elements in FIGS. 1A and 1B and FIG. 5. As evident from a comparison of FIGS. 1A and 1B and FIG. 5, with the fluorescence detector according to the present embodiment, a light beam restriction unit 6 and a condensing lens 7 are disposed between flow cell 3 and the fluorescence side spectrometer 4. The light beam restriction unit 6 has an aperture 6a (or 6b) of a predetermined length in the passage direction of excitation light Lex (in the horizontal direction in FIG. 1) so that, of the fluorescence that is emitted by specimen solution S in flow cell 3, only the fluorescence that passes through aperture 6a (6b) is led to the condensing lens 7 where it is condensed by condensing lens 7 and is led via concave mirror 12 to the fluorescence side spectrometer 4. At the fluorescence side spectrometer 4, the wavelength of the fluorescence that passes through incident slit 41 is dispersed by a concave diffraction lattice 42 so that only the fluorescence with a specific wavelength passes through an exit slit 43 and reaches the detector 5.

FIG. 1B shows the case where an aperture 6a with a long length in the passage direction of the excitation light Lex is installed on light beam restriction unit 6. FIG. 1A shows the case where an aperture 6b with a short length in the passage direction of the excitation light Lex is installed on the light beam restriction unit 6. The width of apertures 6a and 6b in a direction orthogonal to the plane of the paper [on which the figure is drawn] is the same between the two. With the example shown in FIG. 1B, almost all of the fluorescence that is emitted by the specimen solution S in flow cell 3 passes through the condensing lens 7 and reaches the fluorescence side spectrometer 4. This configuration is substantively the same as the typical previous fluorescence detector shown in FIG. 5. In contrast to this, with the example shown in FIG. 1A, because aperture 6b is positioned only at the incident end of the excitation light Lex, the fluorescence that is emitted in a region away from the incident end of the excitation light Lex, i.e., the fluorescence that is emitted after the excitation light Lex has travelled some distance through the specimen solution S, is blocked by the light beam restriction unit 6 and does not become incident on the condensing lens 7. As evident from FIG. 1A, this means that only the fluorescence that is emitted in a region close to the incident end of the excitation light Lex is reflected in the fluorescence intensity that is detected by the detector 5. In other words, if the specimen concentration is high, the fluorescence that is emitted in regions where the excitation light Lex does not fully reach because of its absorption during passage [through the sample specimen] is discarded and is not reflected in the fluorescence intensity.

The transparent flow cell 3 such as that shown in FIG. 2 is housed inside a cell housing 10 that is opaque. The excitation light is made incident to the incident end surface of the flow cell 3 by condensing lens 11 that is incorporated in the cell housing 10. Although not illustrated in FIG. 2, an inlet opening and an outlet opening for the specimen solution are formed on the side surface (the facing surface and the rear-facing surface in FIG. 2) of the flow cell 3. The fluorescence adjustment optical unit 20 which integrates the light beam restriction unit 6 and the condensing lens 7 in a single component is removably installed on the cell housing 10. The selection of apertures 6a and 6b shown in FIGS. 1A and 1B featuring different length in the passage direction of the excitation light Lex is accomplished by the replacement of the fluorescence adjustment optical unit 20.

Figure 3A:
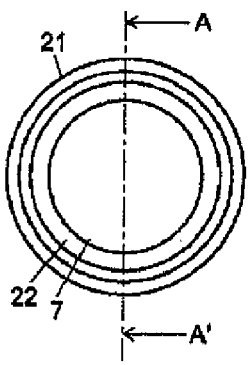
FIGS. 3A-3D shows an external views and a sectional views of the fluorescence adjustment optical unit in FIG. 2.
Figure 3B:
Figure 3C:
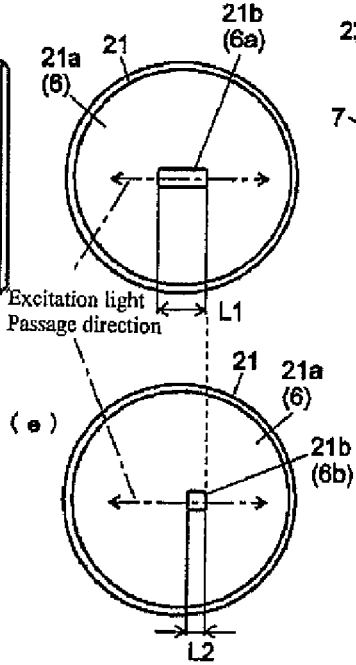
Figure 3D:
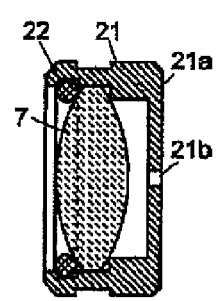

FIGS. 3A, 3B and 3C respectively show a left side view, a front view and a right side view of the fluorescence adjustment optical unit 20. FIG. 3D shows a sectional view taken along line a-a and as viewed in the direction of the arrows in FIG. 3A. These figures show a standard unit that is suited for measuring specimens having a relatively low concentration.

The fluorescence adjustment optical unit 20 is cylindrically shaped with a bottom surface and includes a lens holder 21 made of resin, a convex lens that serves as condensing lens 7 and an elastic O-ring 22. With the fluorescence adjustment optical unit 20 installed on the cell housing 10, the bottom plate 21a of the lens holder 21 contacts the flow cell 3, and the bottom plate 21a serves as the light beam restriction unit 6. A hole 21b that is formed in the bottom plate 21a serves as the aperture 6a (or 6b). The condensing lens 7 is housed inside the lens holder 21. The O-ring 22 fits inside a groove that is formed on the inner peripheral wall of the lens holder 21 so that the O-ring 22 pushes on the condensing lens 7 and holds it in place.

In FIG. 3C, the length L1 of the hole 21b (aperture 6a) is 4 mm. On the other hand, with FIG. 3E which is a right side view of the unit used for measuring specimens of a high concentration, the length L2 of the hole 21b (aperture 6b) is 1.5 mm which is less than L1. As evident from FIG. 2, when the length of the hole 21b (apertures 6a, 6b) differs, the range of the angle of incidence of the fluorescence to condensing lens 7 and the range of positions where fluorescence is generated become different. However, the concave mirror 12 must condense the fluorescence with respect to the incident slit 41 that is always positioned in the same place. Because of this, the optical properties (such as the focal distance) of the condensing lens 7 and optical layout such as the distance between the light beam restriction unit 6 and the condensing lens 7 must be changed in accordance with the different length of the hole 21b. To explain, the light beam restriction unit 6 and the condensing lens 7 form a pair so that the replacement of the fluorescence adjustment optical unit 20 necessarily entails the replacement of the pair including the light beam restriction unit 6 and its matching condensing lens 7.

Figure 4:
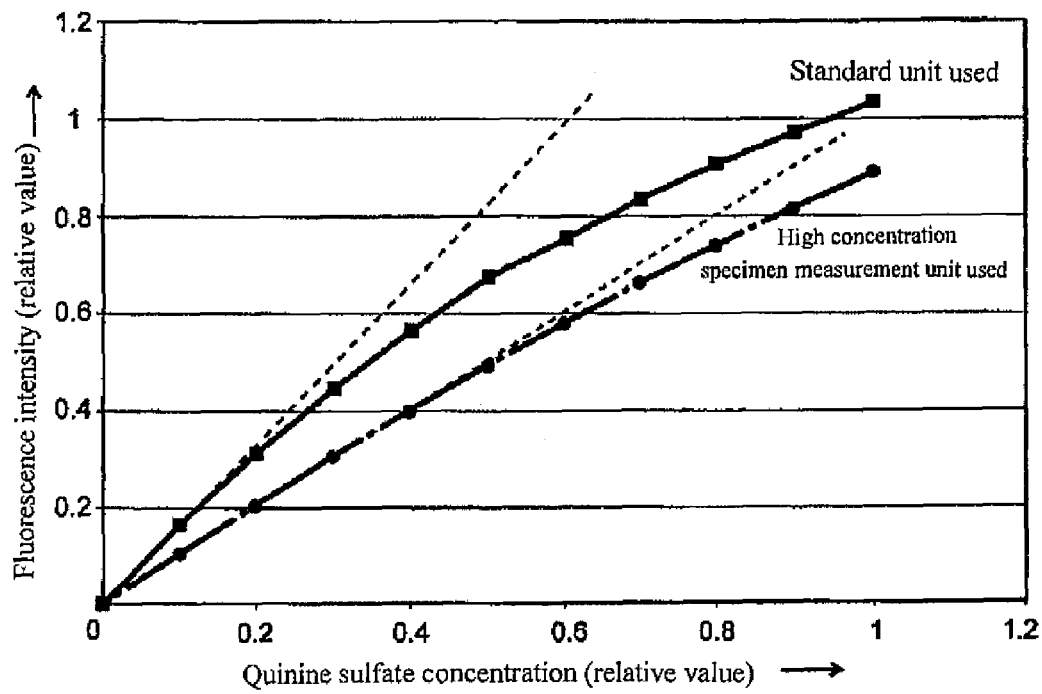
FIG. 4 is a graph that shows how the relationship between fluorescence intensity and specimen concentration differs depending on the length of the aperture of the light beam restriction unit.

FIG. 4 is a graph showing the relationships that were actually measured between specimen concentration and fluorescence intensity using the afore-described two types of units, the high-concentration specimen measurement unit (FIG. 3E) and a standard unit (FIG. 3C). The specimen that was used was quinine sulfate. In the figure, the dotted lines show a linear relationship to better illustrate the curvature of the two curves.

When the high-concentration specimen measurement unit is used, a part of the fluorescence that is emitted by the specimen solution S is intentionally blocked by the light beam restriction unit (bottom plate 21a) 6. Because of this, the fluorescence intensity is generally lower than that obtained when the standard unit is used. However, the non-linearity is greater with the standard unit and the deviation from a linear relationship is pronounced in the relatively high concentration range. In contrast to this, with the high-concentration specimen measurement unit, the linearity is improved, and a good linear relationship is maintained even in the high concentration range. As shown in FIG. 1A, the reason is that when the high-concentration specimen measurement unit is used, the fluorescence that is generated in a region located far away from the incident end of the excitation light is not reflected in the final fluorescence intensity so that the effect of the absorption of the excitation light Lex by the specimen solution S is substantially not reflected in the relationship between specimen concentration and fluorescence intensity. This means that when the high-concentration specimen measurement unit is installed on the cell housing 10 and a calibration curve is prepared using a specimen of a known concentration and the calibration curve is used to quantify an unknown specimen, the specimen concentration is accurately calculated from the fluorescence intensity even in a high concentration range.

The afore-described calibration curve can be used even in a low concentration range. However, as afore-described, when the high-concentration specimen measurement unit is used, the fluorescence intensity is itself decreased somewhat which does not work favorably in terms of the S/N ratio and the like in a low concentration range. Hence, if the specimen concentration is relatively low, it is better to use the standard unit. To explain, by installing the standard unit on the cell housing 10 and using a specimen of a known concentration to prepare a calibration curve and then using the calibration curve to quantify an unknown specimen, the specimen concentration can be calculated from the fluorescence intensity with a high accuracy and high sensitivity.

To further explain, if, in performing a measurement using the fluorescence detector of the present embodiment, it is known in advance that the concentration of the specimen to be measured is high, the person performing the analysis should install the high-concentration specimen measurement unit onto the cell housing 10 to perform the measurement. On the other hand, if the concentration of the specimen to be measured is known to be low in advance or if the specimen concentration is completely unknown, the person performing the analysis should install the standard unit on the cell housing 10 to perform the measurement. In the case of the latter, if the measurement results of the unknown specimen show that the specimen concentration is high, it is advisable to install the high-concentration specimen measurement unit on the cell housing 10 and to repeat the task from the preparation of the calibration curvet to performing the measurement so as to increase the quantification accuracy. In this way, even when the specimen concentration is high, the concentration can be calculated with a higher accuracy as compared to previous [fluorescence detectors].

With the afore-described embodiment, the aperture length in the passage direction of the excitation light Lex were provided in two types, but it should be obvious that the number of types of aperture length can be further increased. Furthermore, instead of replacing the fluorescence adjustment optical unit itself, it is possible to use a configuration wherein the length of the aperture of the light beam restriction unit 6 is manually or automatically switched with the condensing means such as the condensing lens being changed in synchrony.

Furthermore, the afore-described embodiment is just one example of the present invention, and it should be obvious that various modifications, changes and additions can be made to the gist of the present invention without deviating from the scope of the claims.

EXPLANATION OF THE NUMERICAL REFERENCES

1. Light source unit
2. Excitation side spectrometer
3. Flow cell
4. Fluorescence side spectrometer
5. Detector
6. Light beam restriction unit
6a, 6b. Aperture
7. Condensing lens
S. Specimen solution
10. Cell housing
11. Condensing lens
12. Concave mirror
20. Fluorescence adjustment optical unit
21. Lens holder
21a. Bottom plate
21b. Hole
22. O-ring

What is claimed is:

1. A fluorescence detector comprising:
a specimen cell for holding a specimen therein;
an excitation optical system for irradiating said specimen cell with an excitation light;
a fluorescence measurement optical system for detecting the fluorescence that is emitted by the specimen in response to the excitation light; and
a fluorescence adjustment optical system comprising a light beam restriction means that is installed close to said specimen cell so as to block the fluorescence that is emitted by the specimen but does not pass through the aperture and having an aperture of a predetermined length in the passage direction of the excitation light in a specimen cell; a condensing means for condensing the fluorescence that passes through the aperture of the light beam restriction means and leading the fluorescence to the fluorescence measurement optical system, said light beam restriction means and said condensing means provided as a pair; and a mechanism for replacing or switching the fluorescence adjustment optical system so that the length of the aperture can be selected from any one of at least 2 types or more.

2. The fluorescence detector according to claim 1 wherein said light beam restriction means comprises an aperture through which fluorescence emitted from the incident end of the excitation light to said specimen cell can pass regardless of the aperture length.

3. The fluorescence detector according to claim 2 wherein said fluorescence adjustment optical system is an integrated component such that at least two types or more of the length of said aperture is selectable by the replacement of said component.

* * * * *